United States Patent [19]

Walker et al.

[11] 4,012,221

[45] Mar. 15, 1977

[54] SLOW RELEASE COPPER TOXICANT COMPOSITIONS

[75] Inventors: Katherine E. Walker, Akron; Nathan F. Cardarelli, Barberton, both of Ohio

[73] Assignee: International Copper Research Association Inc., New York, N.Y.

[22] Filed: May 13, 1975

[21] Appl. No.: 577,051

[52] U.S. Cl. .......................................... 71/66; 71/67; 71/97; 71/DIG. 1; 424/19; 424/22; 424/83; 424/141; 424/143

[51] Int. Cl.² ............................................. A01N 11/04

[58] Field of Search ............. 71/66, 67; 424/19, 22, 424/83

[56] References Cited

UNITED STATES PATENTS

| | | | |
|---|---|---|---|
| 2,551,446 | 5/1951 | Marks | 71/67 |
| 3,336,129 | 8/1967 | Herrett et al. | 71/67 |
| 3,336,155 | 8/1967 | Rowe | 424/19 |
| 3,417,181 | 12/1968 | Cardarelli | 424/229 |
| 3,495,000 | 2/1970 | Merabi et al. | 424/22 |
| 3,639,583 | 2/1972 | Cardarelli et al. | 424/125 |
| 3,753,676 | 8/1973 | Halley | 71/67 |
| 3,767,809 | 10/1973 | Cardarelli | 424/304 |

OTHER PUBLICATIONS

Singer, "Removal of Scale Formed During Heat, etc.," CA 56 p. 242 (1962).

*Primary Examiner*—Glennon H. Hollrah
*Attorney, Agent, or Firm*—Pennie & Edmonds

[57] ABSTRACT

A method and composition for destroying disease transmitting trematode hosts over a sustained period of time by treatment with a controlled release toxicant composition. The composition comprises a water-soluble, inorganic copper salt capable of releasing copper ions in water which is substantially uniformly dispersed in a moderately crosslinked elastomer in which the copper salt is insoluble. The composition, when contacted with water, allows for the controlled and sustained release of copper ions to cause chronic intoxication and eventual destruction of the molluscan target.

8 Claims, No Drawings

SLOW RELEASE COPPER TOXICANT COMPOSITIONS

BACKGROUND OF THE INVENTION

This invention relates to certain copper toxicants and the dissemination of them in a sustained and controlled manner to destroy disease spreading trematode hosts. It is well known that various molluscan species, such as snails, serve as hosts to trematode parasites which infect both man and lower animal species with various diseases. Man can be infected with debilitating Shistosomiasis from various trematode parasites including S. hematobium, S. mansoni, S. japonicum, and S. dermatitis. Other trematodes are causative agents of Fascioliasis, a disease which effects various animals such as domestic horses, cattle and sheep.

Control of the diseases caused by trematodes, such as Shistosomiasis and Fascioliasis, have been conventionally done through medical programs, sanitary engineering and chemical treatment. Medical programs are expensive to the point of being out of economic reach for most of the affected areas. Further, although various drugs are known which will stop the infection within an individual, the treatment cannot stop the disease causing cycle in that immunity cannot be conferred and the "cured" individual usually becomes reinfected upon reexposure to the trematode-infected waters. Sanitary engineering, including sanitary facilities, water purification, concrete lined irrigation canals, etc., are also far too expensive to undertake on the massive scale which is required.

The primary method of controlling diseases carried by the various trematodes is the destruction of the host molluscan by the application of chemical agents to the infected area, such as a waterway. These molluscicides, include copper salts, sodium pentachlorophenate, N-trityl-morphine, niclosamide salts and organo tin compounds, are applied to the infested waterways as solutions, emulsions, wettable powders or granules in conventional manners. The treated water bodies are toxic for only short periods of time due to the nonpersistent nature of the molluscicide toxicant which chemically interact with dissolved minerals and gases, are absorbed by suspended matter, and undergo biodegradation. Molluscicide effective life is further shortened in flowing water systems by the dilution of fresh water inflow. The relatively low effective life of the molluscicide toxicant requires frequent application of massive dosages of the toxicant material. Although such treatment effectively destroys the host molluscan it is also detrimental to piscine life and other nontarget elements of the biota. Further, it is known that the target molluscans are capable of detecting the toxicants at the high level used and are able to evade mortality by burrowing in the mud or leaving the treated water body, and returning after detoxification to reinfest the now cleared waterway. The net result is the necessity for systematic, periodic retreatment.

Various compounds, including those of copper, have also been previously used as a pesticide to control undesired aquatic plant life. The conventional application of large dosages of these compounds has known detrimental effects on desired plant and animal life as discussed above.

Slow releasing toxicant compositions are presently known which have a long term biocidal effectiveness. While conventional treatment results in acute intoxification and rapid mortality of the target as well as other aquatic life, the slow release toxicant compositions are able to establish a constant level of intoxification of the water body leading to mortality of the target through subacute or chronic manifestations. The slow releasing toxicant compositions, such as those taught in U.S. Pat. Nos. 3,639,583; 3,417,181; and 3,767,809, utilize various organic toxicants, including organo tin and organo phosphorus compounds. These compositions consist of toxicant-elastomeric matrix which have certain solubility relationships which allow for the slow loss of the toxicant into the surrounding waters through a diffusion-dissolution mechanism. The long term action provided by these known compositions results from the physical mechanism of solubility equilibrium and requires that the toxicant agent be soluble in the elastomeric material utilized. The toxicant release is thereby governed by a solubility equilibrium wherein the loss of toxicant material near the elastomeric matrix surface-water interphase leads to solution disequilibrium within the matrix and the migration of the internal molecules of elastomer-soluble toxicant toward the depleted surface area. The net result is a continuous loss of toxicant in accordance with the classical diffusion principles. These toxicant compositions have the drawback of being limited to toxic materials which are soluble in the elastomeric matrix and relatively insoluble in water. Such toxic materials are relatively expensive and may present a human health hazard in their formation, handling and use.

Copper compounds have been previously utilized as a pesticidal agent and more specifically as a molluscicide. The copper compounds are preferred over various other known molluscicide materials due to their relatively low cost and low toxic properties to humans but when presently utilized require frequent application of large dosages to be effective. The present copper toxicants have heretofore not been found useful in sustained release application because of their known insolubility in the elastomeric matrixes.

SUMMARY OF THE INVENTION

It has been presently found that water-soluble, elastomer insoluble copper salts which are capable of releasing copper ions on contact with water can be incorporated into their insoluble elastomeric matrix and provide a sustained release composition which is effective in destroying various molluscan species, such as snails, which serve as hosts to various trematode parasites. The present composition has also been found to be an effective herbicidal composition capable of controlling aquatic pest plant growth.

This invention relates to novel compositions and methods of using the same for destroying target pest plants and disease transmitting animal hosts by applying to infested water bodies a water-soluble inorganic copper salt in powder form which is substantially uniformly dispersed in a moderately crosslinked elastomeric matrix. The present composition is capable of releasing, over a sustained period of time, a controlled amount of copper toxicant to cause chronic intoxication of the target while being substantially harmless to piscine animal life.

DETAILED DESCRIPTION OF THE INVENTION

The present invention relates to a sustained release copper composition which can effectively destroy hosts of disease transmitting trematodes, such as those of the Schistosoma and Fasciola genus while being substantially harmless to other aquatic animal life. The present compositions permit a controlled release of copper toxicant in concentrations which cause chronic intoxication and ultimately the death of the target host. Further, the present compositions are useful as a herbicidal agent for pest aquatic plants.

The present composition comprises a moderately vulcanized elastomer which contains substantially uniformly dispersed therein a powdered water soluble inorganic copper salt which is capable of releasing copper ions when contacted with water and which is insoluble in the elastomeric matrix. The compositions of this invention when contacted with water allow for the controlled and sustained release of copper ions to the infested waterways.

Any inorganic copper salt which is water soluble and substantially insoluble in the elastomeric material in which it is bound can be utilized. The copper salt should be capable of releasing the copper ions when it is contacted with water. The utilization of inorganic copper salts are more advantageous than the various known organic toxicants from both an economic and health standpoint. The salts are far less expensive, more readily available, and are much less harmful to aquatic life, in general. Furthermore, fish and most other animals can tolerate and indeed need small amounts of copper for nutritional purposes. Thus, animal and most plant life are not adversely effected by the small amounts of toxicant presently used and the environmental contamination is thus negligible.

The copper salts found useful as toxicants in the present invention are those that are water-soluble, elastomer insoluble and capable of releasing copper ions when in contact with water. Such copper salts include hydrated copper sulfate, such as copper sulfate pentahydrate and copper sulfate monohydrate, anhydrous copper sulfate, and copper halides, such as copper chloride, copper bromide, copper fluoride and the like. The preferred compounds being the hydrated copper sulfate with copper sulfate monohydrate being the most preferred.

The copper salts should be in powder form which all form a substantially uniform distribution throughout the matrix. The powder should preferably be capable of passing through a No. 20 Standard Sieve (Tyler Series). The use of such powdered material allows for sustained release of the toxicant copper salt by allowing the particles of powder, or small agglomerations of the same, to be encapsulated in the elastomer material. The unexpected sustained release of the copper toxicant is believed to be attributable to the permeability of the water into an encapsulated cell, leaching the water-soluble salt therefrom and the water in the resultant cell then attacks the surrounding cells by permeating the elastomer wall and again leaching. The successive process of permeating the elastomer walls surrounding the toxicant particle and leaching the toxicant therefrom results in a sustained release composition. Further, the copper salt located internally in the matrix is released to the infested waters in a sustained manner because it is required, once contacted with water, to be liberated by the tortuous cellular path formed by previously leached material.

The elastomers found useful in the practice of this invention are rubbers which are water permeable to a slight extent and which may also be slightly biodegradable. The degree of water permeability need only be that which allows for the passage of sufficient amounts of water through the elastomeric matrix to allow for the leaching of the copper salts from the matrix composition. The elastomers include ethylene-propylene copolymers, styrene-butadiene copolymers, isobutylene-isoprene copolymers, polychloroprene or natural rubber with the copolymer of ethylene-propylene being preferred. The useful elastomers are vulcanizable or readily crosslinked with conventional agents such as sulfur, sulfur-containing compounds, metal oxides, peroxides, amines and the like. Examples include elemental sulfur, mercaptobenzothiazol, benzothiazol disulfide, tetramethylthiuram disulfide, and the like.

The compositions of this invention are prepared by mixing the copper toxicant in powdered form with the uncured elastomer material. Basic or conventional rubber compounding techniques and equipment can be used in the preparations of the mixture. The powders are continuously mixed with the unvulcanized elastomer until essentially uniformly dispersed therein. Other additional ingredients, such as fillers, lubricants, vulcanizing agents, etc., can be incorporated into the elastomer at this time. The controlled release pesticidal compositions of this invention are to be formed by slightly vulcanizing the elastomeric matrix to entrap the copper toxicant therein. Such slightly vulcanized compositions are considerably more effective than unvulcanized or highly vulcanized materials. Because the toxicant material is admitted into the water body by a leaching process, the exact degree of vulcanization is not critical. The dependence of copper loss does not vary to any large degree in relation to the degree of a vulcanization or crosslinking of a moderately vulcanized product.

The controlled release copper toxicant compositions of this invention are in the form of slightly vulcanized elastomeric matrix. They may be in a wide variety of shapes, such as chunks, pellets, strips, or very long tapes depending on the service required. The pellets, for example may be smaller in size and weight than a kernel of corn, or may be several centimeters in diameter. These compositions may be molded to any configuration or article in accordance with conventional techniques in the rubber manufacturing art. In whatever form, these compositions are relatively safe and non-toxic to humans and higher animal forms while they are in storage or in shipment to the site of use and they remain stable and effective for an indefinite period of time. To distribute these pesticides for use, the elastomer compositions are merely inserted into the body of infested water to be treated. They do not require any special distribution in the water. After immersion the water progressively leaches out the toxicant from the elastomeric agent.

The formed composition can have from about 75 to about 400 parts by weight of inorganic copper salt in the elastomeric matrix per 100 parts of elastomer material. The amount of toxicant to be present in the composition is to be determined predominantly on the rate of toxicant to be released over a sustained period of time. The amount of toxicant, the type of elastomer utilized and the surface area of the matrix will generally determine the rate of release of a particular toxicant. The rate of loss being directly proportional with the amount of toxicant utilized and with the surface area of the copper-ladened elastomeric matrix. The exact rate of any particular copper salt which is incorporated into a particular elastomer can be determined by conventional methods well known to those skilled in the art.

It has been found that in bodies of water where other aquatic life are present, the rate of toxicant loss to the infested water should be from about 0.001 ppm per day to about 0.05 ppm per day with from about 0.001 ppm to about 0.03 ppm per day being preferred. Such concentration of toxicant will destroy the host molluscan by chronic intoxication but will not readily effect the other desired non-target aquatic life. It is realized that greater rates of loss of toxicant may be permitted where aquatic life is not in jeopardy such as when the controlled release copper pesticide composition is utilized in irrigation ditches and the like. The gradual accumulation of copper toxicant over several days or even several weeks within the target molluscan leads to physiological impairment which terminates in death. Since such accumulation is slow and arises from ultra low concentration of toxicant, the target molluscan does not detect its presence and therefore, does not take the avoidance behavior normally observed with the conventional application of massive dosages of toxicant. Consequently, area wide treatment is far more thorough. The net overall effect is a dramatic increase in the between treatment interval and the possibility of permanent destruction of the disease breeding host.

When the controlled release copper toxicant composition is exposed to water, the gradual release of copper ions may lead to a slow buildup of an insoluble film on a matrix surface. This film is normally copper carbonate which, as its thickness increases, acts to increasingly prevent the release of the copper toxicant from the matrix. Such compositions have, therefore, a shortened period of sustained release of two to three months. It has been found that the addition of small amounts of ammonium sulfate to such compositions effectively changes the surface pH conditions surrounding the matrix which retards or prevents the formation of the insoluble film. The sustained release period is thus increased by several months. The ammonium sulfates may be added simultaneously with the copper salt in the compounding of the elastomeric matrix and the loss of ammonium sulfate from the matrix probably occurs by the same mechanism which causes the release of the copper salt materials. The ammonium salt is of value in the presently claimed invention only in order to alter the chemical situation at the elastomer-water interphase and does not have any pesticidal or toxic effects. The ammonium sulfate may be added in amounts of up to about 5% by weight of the elastomeric composition. Greater amounts may be added although producing little or no additional effects.

The present composition can contain, in addition to the copper salt and elastomer, other ingredients such as lubricants, fillers and the like. Carbon black and zinc oxide are useful fillers for reinforcement purposes. Further, zinc oxide also aids in preventing over-vulcanization of the matrix. Processing oils and other lubricating materials common to the rubber processing art can be incorporated into the matrix to aid in the production of the final compositions of the present invention.

It has been presently found that the copper compositions presently disclosed are also herbicidal agents which effectively control the growth of pest plants while being substantially unharmful to piscine life. The presently disclosed copper compositions have been found to be especially effective in controlling the pest plants of the genus Elodea, Vallisneria, Hydrilla and Myriophyllum. Examples of each include *E. Canadenais, V. americana, H. verticillata* and *M. spicatum*. The sustained release copper compositions are used in the same manner as described above for pesticidal activity.

The following examples are set forth for the purposes of illustration only and are not to be construed as limitations on the present invention except as set forth in the appended claims. All parts and percentages are by weight unless otherwise indicated.

EXAMPLES I–V

Propylene-Ethylene Elastomer Base Compositions

The components listed in Table I below were mixed together using a Banbury Mixer in amounts indicated until they were substantially uniformly distributed in the elastomer. The resultant compositions were vulcanized at 290° F. for 30 minutes according to conventional rubber processing techniques.

Table I

|  | Ex. I | Ex. II | Ex. III | Ex. IV | Ex. V |
|---|---|---|---|---|---|
|  | (Parts by weight) | | | | |
| Epcar 5465 | 100 | 100 | 100 | 100 | 100 |
| Carbon Black (HAF grade, 45 mu) | 10 | 10 | 10 | 50 | 50 |
| Zinc Oxide | 3 | 3 | 3 | 3 | 3 |
| Stearic Acid | 0.5 | 0.5 | 0 | 0 | 0 |
| Hydrocarbon Oil (Sunthene Oil No. 4240) | 5.0 | 5.0 | 0 | 0 | 0 |
| MBT (Mercaptobenzothiazol) | 0.2 | 0.2 | 0.2 | 0.2 | 0.2 |
| TMTD (Tetramethylthiuram disulfide) | 1.0 | 1.0 | 1.0 | 1.0 | 1.0 |
| Sulfur | 1.0 | 1.0 | 1.0 | 1.0 | 1.0 |
| $CuSO_4$ | 370 | 0 | 0 | 0 | 0 |
| $CuSO_4 \cdot 5H_2O$ | 0 | 200 | 0 | 0 | 0 |
| $CuSO_4 \cdot H_2O$ | 0 | 0 | 118.2 | 157.2 | 135.2 |
| Ammonium Sulfate | 0 | 0 | 3 | 2 | 0 |

EXAMPLES VI–IX

Styrene-Butadiene Elastomer Base Compositions

The components listed in Table II were mixed in a Banbury Mixer until a substantially uniform composition was formed. The compositions were vulcanized at 293° F. for 50 minutes.

Table II

| Components | Ex. VI | Ex. VII | Ex. VIII | Ex. IX |
|---|---|---|---|---|
| | (Parts by weight) | | | |
| Styrene-Butadiene Co-polymers (Ameripol 1503) | 100 | 0 | 0 | 0 |
| Styrene-Butadiene Co-polymers (Ameripol 4615) | 0 | 100 | 0 | 0 |
| Styrene-Butadiene Co-polymers (Ameripol 1510) | 0 | 0 | 100 | 100 |
| HAF Black | 15 | 15 | 15 | 15 |
| Stearic Acid | 1 | 1 | 1 | 1 |
| Sulfur | 1.5 | 1.5 | 1.5 | 1.5 |
| MBT | 1 | 1 | 1 | |
| Zinc Oxide | 3 | 3 | 3 | 3 |
| $CuSO_4 \cdot H_2O$ | 0 | 0 | 182 | 0 |
| $CuSO_4 \cdot 5H_2O$ | 346 | 486 | 0 | 0 |
| $CuSO_4$ | 0 | 0 | 0 | 182 |

EXAMPLE X

A composition was formed by mixing the following components in a Banbury mixer until a substantially uniform composition is formed.

| Components | Parts |
|---|---|
| Natural Rubber | 100 |
| HAF Black | 7.0 |
| Zinc Oxide | 2.0 |
| Stearic Acid | 0.3 |
| PBNA (phenyl-B-naphthylamine) | 0.5 |
| Sulfur | 2.0 |
| MBT | 1.0 |
| BTD (Benzothiazol disulfide) | 1.0 |
| Copper Sulfate Pentahydrate | 455 |

The composition was vulcanized at 290° F. for 30 minutes.

EXAMPLES XI-XII

Polybutadiene Elastomer Base Compositions

The components listed in Table III were mixed in a Banbury Mixer until a substantially uniform composition was formed. The compositions were vulcanized at 290° F. for 30 minutes.

Table III

| Component | Ex. XI | Ex. XII |
|---|---|---|
| Polybutadiene | 100 | 100 |
| Carbon Black (FEF grade, 80 m$\mu$) | 15 | 15 |
| Zinc Oxide | 1.0 | 1.0 |
| Sulfur | 1.5 | 1.5 |
| MBT | 1.0 | 1.0 |
| $CuSO_4 \cdot 5H_2O$ | 178 | 0 |
| $CuSO_4$ | 0 | 52 |

EXAMPLE XIII

Adult *Biophalaria glabrata* snails, the host of *S. mansoni* trematodes, were exposed in replicates of 10 snails to 10 mg. pellets formed from slow release copper compositions of Examples I through XII. Exposure was performed in 1000 cc glass containers using aquaria water. The exposure was limited to ten day periods. Fatality is noted by direct observation except in questionable cases where the subject is microscopically examined for heart beat through its transparent shell. The results are given in Table IV below.

Table IV

| Composition of Example | Mo. I | Mo. II | Mo. III | Mo. IV |
|---|---|---|---|---|
| 1 | 100% | 100% | 100% | 0% |
| 2 | 100% | 100% | 100% | 0% |
| 3 | 100% | 100% | 80% | 13% |
| 4 | 100% | 100% | 100% | 70% |
| 5 | 100% | 100% | 100% | 90% |
| 6 | 100% | 67% | 100% | 17% |
| 7 | 100% | 100% | 97% | 73% |
| 8 | 97% | 84% | 100% | 100% |
| 9 | 100% | 47% | 90% | 100% |
| 10 | 100% | 100% | 60% | — |
| 11 | 100% | 100% | 100% | 17% |
| 12 | 100% | 97% | 100% | 43% |
| Controls | 0% | 3% | 3% | 7% |

The results clearly show that each of the compositions gave a sustained release of copper toxicant causing complete or at least substantial destruction over a period of time.

EXAMPLE XIV

Adult *B. glabrata* were exposed to a natural milieu created by placing a highly organic soil in the bottom of a test aquaria, planting various aquatic weeds therein, aerating, and maintaining a high mineral content in the waters.

In order to simulate natural conditions a 10% per day water change rate is maintained in each test aquaria. Dead snails and fish are removed daily to prevent substantial fouling of the water. Mortality observations are made daily. At the end of each 30 day period all still living snail and fish specimens are removed and new unexposed animals added. The test pellet is suspended midway in the water to eliminate variables arising from silting over, etc.

The following table illustrates snail mortality over an extended treatment period. Dosages used are 100 ppm pellets. The test pellets being continuously exposed to water. The results are given in Table V below.

Table V

| | Microenvironmental Bioassay Of Snail Mortality | | | |
|---|---|---|---|---|
| Composition of Example | Mo. I | Mo. II | Mo. III | Mo. IV |
| 1 | 100% | 100% | 30% | — |
| 2 | 94% | 73% | 97% | 80% |
| 3 | 100% | 100% | — | — |

Table V-continued

| Composition of Example | Microenvironmental Bioassay Of Snail Mortality | | | |
|---|---|---|---|---|
| | Mo. I | Mo. II | Mo. III | Mo. IV |
| 4 | 73% | 90% | — | — |
| 5 | 100% | — | — | — |
| 6 | 100% | 94% | — | — |
| 7 | 100% | 100% | — | — |
| 8 | 100% | 73% | 87% | 90% |
| 9 | 100% | 94% | — | — |
| 10 | 100% | 100% | 60% | 63% |
| 11 | 100% | 90% | — | — |
| 12 | 100% | 100% | — | — |
| Controls | 7% | 7% | 5% | 6% |

Select data from beyond the fourth month indicates that various formulations continue to release copper ion at biologically effective rates as shown in Table VI.

Table VI

| Composition of Example | Microenvironmental Bioassay Of Snail Mortality | | |
|---|---|---|---|
| | Month V | Month VI | Month VII |
| 2 | 87% | 97% | 14% |
| 8 | 100% | 37% | — |

EXAMPLE XV

In microenvironments similar to that described in Example XIV above were added 10 adult *L. reticulata* (guppies) and 10 adult *B. glabrata*. Samples of slow release composition of Example II were made into pellets. The rate of copper ion release for each of the samples was measured using standard photometric techniques. The various slow release pellets were added to each of the prepared environments. The effect on the aquatic life is given in Table VII below.

Table VII

| Dosage | | Long Term Exposure to Copper Ion Mortality (Accumulative) | | | | | | |
|---|---|---|---|---|---|---|---|---|
| | | 5 Day | | 30 Day | | 60 Day | | 120 Day | |
| copper Ion | | L.R. | B.G. | L.R. | B.G. | L.R. | B.G. | L.R. | B.G. |
| 0.65 | ppm/day | 8% | 100% | 42% | 100% | 94% | 100% | 96% | 100% |
| 0.13 | ppm/day | 6% | 22% | 20% | 86% | 20% | 100% | 30% | 100% |
| 0.050 | ppm/day | 0% | 10% | 8% | 38% | 10% | 87% | 10% | 100% |
| 0.013 | ppm/day | 0% | 2% | 2% | 18% | 2% | 58% | 2% | 74% |
| 0.0026 | ppm/day | 0% | 0% | 0% | 2% | 0% | 28% | 0% | 38% |
| 0.0000 | (Control) | 2% | 0% | 4% | 4% | 4% | 4% | 4% | 12% |

EXAMPLE XVI

Microenvironments were made as described in Example XIV in which various aquatic pest weeds were planted. The microenvironment also contained *L. reticulatus*. Controlled release compositions of Examples I to XII were separately placed in each of the microenvironments. Treatment rate was 100 ppm (pellet). The average results over a two month test period using 36 plants per test is recorded in Table VIII below. Observations were continued on the pest plant *E. canadensis* for a total of six months.

Table VIII

| Mortality | Plant Classification* | | | |
|---|---|---|---|---|
| | E | H | V | M |
| Month I | | | | |
| Plant | 83% | 100% | 100% | 100% |
| Fish | 9% | 5% | 17% | 7% |
| Month II | | | | |
| Plant | 84% | 51% | 92% | 65% |
| Fish | 7% | 5% | 2% | 3% |
| Month III | | | | |
| Plant | 100% | — | — | — |
| Fish | 7% | — | — | — |
| Month IV | | | | |
| Plant | 91% | — | — | — |
| Fish | 5% | — | — | — |
| Month V | | | | |
| Plant | 80% | — | — | — |
| Fish | 1% | — | — | — |
| Month VI | | | | |
| Plant | 95% | — | — | — |
| Fish | 0% | — | — | — |

*Legend
| Code | Generic Name | Common Name |
|---|---|---|
| E = | Elodea canadensis | Elodea |
| H = | Hydrilla verticillata | Hydrilla |
| V = | Vallisneria americana | Vallisneria |
| M = | Myriophyllum spicatum | Eurasian Watermilfoil |

While the invention has been described in connection with a preferred embodiment, it is not intended to limit the invention to the particular form set forth, but, on the contrary, it is intended to cover such alternatives, modifications and equivalents as may be included within the spirit and scope of the invention as defined by the appended claims.

What is claimed is:

1. A sustained release toxicant composition comprising a moderately vulcanized elastomeric matrix selected from ethylene-propylene copolymer, styrene-butadiene copolymer, isobutylene-isoprene copolymer, polybutadiene or natural rubber having substantially uniformly dispersed therein up to about 5 parts by weight ammonium sulfate per 100 parts of said elastomer and from about 75 parts to about 400 parts per 100 parts by weight of said elastomer of a water-soluble, elastomer-insoluble inorganic copper compound, said copper compound being capable of releasing copper ions when in contact with water.

2. The composition of claim 1 wherein the copper compound is selected from copper halide, copper sulfate or copper nitrate.

3. The composition of claim 2 wherein the copper compound is copper sulfate monohydrate.

4. The composition of claim 3 wherein the matrix contains up to about 2 parts by weight per 100 parts by weight of elastomer of ammonium sulfate.

5. The composition of claim 2 wherein the copper compound is a copper sulfate.

6. A method of destroying aquatic pest weeds comprising applying to the weed infested waters an effective amount of a composition of claim 1 to liberate sustained quantities of copper compound to kill the weeds.

7. The method of claim 6 wherein the copper compound is selected from copper halide, copper sulfate, or copper nitrate.

8. The method of claim 6 wherein the copper compound is a copper sulfate.

* * * * *